United States Patent [19]

Eguchi et al.

[11] Patent Number: 4,922,104
[45] Date of Patent: May 1, 1990

[54] INFRARED MICROSPECTROMETER

[75] Inventors: Kinya Eguchi, Fujisawa; Kikue Niitsuma, Yokohama; Shigeru Wakena; Masayoshi Ezawa, both of Mobara, all of Japan

[73] Assignee: 501 Hitachi, Ltd., Chiyoda, Japan

[21] Appl. No.: 277,964

[22] Filed: Nov. 30, 1988

[30] Foreign Application Priority Data

Nov. 30, 1987 [JP] Japan .................. 62-300226
Mar. 12, 1988 [JP] Japan .................. 63-59158

[51] Int. Cl.⁵ .............. G01J 3/42; G01W 21/35; G02B 21/00
[52] U.S. Cl. .................. 250/339; 250/347; 350/1.2; 356/73
[58] Field of Search ........ 250/338.1, 339, 347, 250/353, 358.1, 336.1; 356/73, 346; 350/1.1, 1.2, 1.3, 526, 527, 528, 529, 530, 511, 620

[56] References Cited

U.S. PATENT DOCUMENTS

| | | | |
|---|---|---|---|
| 4,594,509 | 6/1986 | Simon et al. | 250/353 |
| 4,712,912 | 12/1987 | Messerschmidt | 356/300 |
| 4,758,088 | 7/1988 | Doyle | 356/346 |
| 4,843,242 | 6/1989 | Doyle | 250/383.1 |
| 4,852,955 | 8/1989 | Doyle et al. | 350/1.2 |

OTHER PUBLICATIONS

"Low-Cost FTIR Microscopy Units Gain Wider Use in Microanalysis", C+EN, Dec. 9, 1985, p. 15, Analect Instruments Publication, Jan. 1986.

*Primary Examiner*—Janice A. Howell
*Assistant Examiner*—Edward Glick
*Attorney, Agent, or Firm*—Kenyon & Kenyon

[57] ABSTRACT

An infrared spectrum measuring microscope apparatus which is suitable for accurately identifying the material at a microfine portion. A sample stage is vertically moved and special optical means are provided in the sample stage for enabling high-sensitivity spectral measurement of a microfine portion of samples of various sizes. The infrared microspectometer of the present invention also enables the chemical species of the sample to be identified by the fluorescence spectrum in addition to the information of the infrared spectrum.

8 Claims, 9 Drawing Sheets

SPECTRAL CHARACTERISTIC
OF DICHROIC FILTER (nm)

INFRARED MICROSPECTROMETER

BACKGROUND OF THE INVENTION

The present invention relates to an apparatus for measuring the infrared spectrum of microfine portions and, more particularly, to an infrared spectrum measuring microscope apparatus which is suitable for accurately identifying the material at a microfine portion.

An infrared spectrum measuring apparatus generally known is composed of an infrared source, a monochrometer for obtaining the infrared intensity for each wavelength component or an interferometer, an infrared detector, a sample chamber, etc. The measurement of the infrared spectrum of a microfine portion is conventionally carried out by a Fourier infrared spectrometer using an interferometer, which has a high sensitivity, in combination with a microscope apparatus such as those discussed by Robart G Messershmidt on pp. 27 to 31 of "The Design, Sample Handling and Application of Infrared Microscopes, ASTM STD 949, American Society for Testing and Materials", Philadelphia (1987)" and on pp. 85 to 87 of "Practical Spectroscopy Series Volume 6, Infrared Microspectroscopy, edited by Robart G Messershmidt", MARCEL DEKKER INC. (1988).

These papers contain the schematic views of a microscope such as those shown in FIGS. 14 and 15. The reference numeral 1 in FIGS. 14 and 15 represents sample stages, 2 and 3 in FIG. 14 and 2 in FIG. 15 represent reflecting objectives, 3 in FIG. 15 represents an ellipsoidal converging mirror for illuminating a sample, 4, 4' in FIG. 14 and 4, in FIG. 15 represent apertures for regulating the measuring visual field, 5 in FIG. 15 a reflecting objective for converging light, and 6 in FIGS. 14 and 15 represents an infrared detector Infrared rays from a Fourier transform infrared spectrometer are represented by the reference numeral 5 in FIG. 14 and 7 in FIG. 15. The infrared spectrum of a sample is generally measured either in a transmission mode or reflection mode. Infrared rays from a Fourier transform infrared spectrometer of a transmission measuring mode are represented by the reference numeral 7 in FIGS. 14 and 15, and infrared rays for measurement in a reflection mode are represented by the reference numeral 5 in FIG. 14, but not shown in FIG. 15. It is assumed to be because infrared rays are projected to the reflecting objective 2 in FIG. 15 through an ellipsoidal mirror 8 in FIG. 15, but details are not described. In this way, since a conventional apparatus utilizes the optical system of an ordinarily used optical microscope, no consideration is given to the size or the like of the object of measurement. That is, since the downward movement of the sample stage 1 in FIG. 15 is restricted by the converging mirror 3 for converging infrared on the sample, and the upward movement of the sample stage 1 is restricted by the reflecting objective 2, the size of the sample to be placed on the sample stage 1 is disadvantageously restricted. In the case of spectral measurement in a transmission mode, the measurable thickness of a sample is 10 to 20 μm by infrared spectral measurement and several cm in an ordinary spectral measurement of a visible region. In this way, spectral measurement in a transmission mode is naturally not intended for a large sample. On the other hand, in the case of spectral measurement in a reflection mode, the surface of a sample is the object of measurement. The conventional apparatus having a limitation in the vertical movement of the sample stage is therefore disadvantageous in that some large samples cannot be placed on the sample stage. This problem produces another serious defect when various jigs for spectral measurement are used in this apparatus.

The problem of the limitation in the vertical movement of the sample stage is produced because neither the converging mirror 3 in FIG. 15 for converging infrared rays on a sample can be lowered in the optical path of infrared rays nor can the reflecting objective 2 be lifted. In addition, measurement of an infrared spectrum or the like is strongly influenced by vapor, carbon dioxide gas, etc. in air. It is therefore necessary to minimize the change of atmosphere over a period of time in all paths for infrared rays. In the conventional apparatus, this point is not taken into any consideration, so that a change of vapor, carbon dioxide gas, etc. in the optical path over a period of time sometimes causes noise in the high-sensitivity measurement of a microfine region of a sample.

As described above, in an infrared spectrum measuring apparatus, the chemical species (functional groups) of a material are identified. That is, since the infrared spectrum of a compound shows the infrared spectrum which is characteristic of the compound, it can be used for identification. However, since most of the objects of measurement are generally mixtures not single materials, the spectra obtained are complicated and difficult to explain. Furthermore, since identification is conventionally made only by an infrared spectrum, it is lacking in accuracy.

That is, the prior art aims only at measuring the infrared spectrum of a microfine portion, and the identification of the material from the spectrum obtained is insufficient and lacking in the accuracy of the identification of the chemical species.

SUMMARY OF THE INVENTION

Accordingly, it is a first object of the present invention to eliminate the above-described problems in the prior art and to provide an infrared microspectrometer which is capable of high-sensitivity spectral measurement of microfine portions of samples having various sizes, in particular, a large size.

It is a second object of the present invention to provide an infrared microspectrometer which is capable of identifying the chemical species of microfine portions of samples with sufficiently high accuracy.

The first object is achieved by an infrared microspectrometer which is capable of measuring and observing a sample in both transmission spectral measuring mode and reflection spectral measuring mode, the infrared microspectrometer comprising a spectrophotometer; a microscope; a detector; and a vertically movable sample stage including an optical means for converting analyzing rays between the spectrophotometer or the light source of the spectrophotometer and the sample stage into parallel rays and an optical means for receiving the rays and projecting them to the sample.

The second object is achieved by an infrared microspectrometer which is capable of measuring the fluorescence spectrum as well as the infrared spectrum of a sample so that the chemical species of the sample may be identified by the fluorescence spectrum in addition to the information of the infrared spectrum.

The operation of the present invention for achieving the first object will be explained with reference to FIGS. 1, 2 and 3. The reference numeral 10 represents a flat mirror for receiving parallel infrared rays with the frequency modulated by the interferometer of a Fourier transform infrared spectrometer. The reflective surface of the flat mirror 10 is changeable for switching over between a reflection mode and a transmission mode. When it is in a reflection measuring mode, the flat mirror 10 directs infrared rays toward a parabolic mirror 11. On the other hand, in a transmission measuring mode, the flat mirror 10 directs infrared rays toward a flat mirror 12. The reflective surfaces are switched by the operation of a lever. The infrared rays are converged on a sample stage 15 by a reflecting objective 13 or an ellipsoidal mirror 14 and projected to the sample stage 15. In the case of a reflection transmission measuring mode, the infrared rays from the parabolic mirror 11 are reflected toward the reflecting objective 13 by an edge mirror 16. The infrared rays from the sample stage 15 pass through the back side of the edge mirror 16 and reach a known infrared detector 171. In the case of a transmission measuring mode, the edge mirror 16 is removed from the optical path.

The reference numeral 18 represents a parabolic mirror, and an ellipsoidal mirror 14 and flat mirrors 19, 20 are mounted on a boat-shaped stage 21 There is another sample stage 23 above the ellipsoidal mirror 14 on the boat-shaped stage 21 in FIG. 1(b). The boat-shaped stage 21 is vertically moved by an up and down-drive unit 22. The infrared rays 24 reflected by the flat mirror 10 are reflected downwardly at a right angle by the flat mirror 12 and become the infrared rays 25. The infrared rays 25 are reflected at a right angle by the parabolic mirror 18 and become infrared rays 26. Since the infrared rays 25 are parallel rays, even if the infrared rays 25 move vertically on the boat-shaped stage 21, they do not exert influence on the optical system thereafter. The above-described structure can dispense with a fixed infrared converging mirror under the sample stage which is required in the prior art, thereby freely moving the sample stage downwardly.

FIG. 2 is an enlarged view of the boat-shaped stage 21. The boat-shaped stage 21 may be made of any material that can transmit the light converged by the reflecting objective 13, or it may have a hole through which the infra-red light converged on the stage can pass. A sample 124 is placed on the stage 23. When a hole is formed in the stage 23, the diameter of the hole must be naturally smaller than the sample 124. The reference numerals 125 and 126 represent screens attached to the lower limit and the upper limit, respectively, of the travel of the boat-shaped stage 21. The screens 125 and 126 are vertically moved in accordance with the vertical movement of the boat-shaped stage 21. The reference numeral 27 denotes a wire for pulling the screens 125, 126 and a weight 28 is attached to the other end of the wire 27. The screen 125 is pulled by a spring 29, thereby keeping balance between both screens 125, 126. In this way, the boat-shaped stage 21 is vertically moved without a load and the air or light outside the microscope is prevented from entering.

The operation of the infrared microspectrometer followed by the vertical movement of the microscope body will now be explained with reference to FIG. 3. Both the incident angle and the reflection angle of infrared rays with respect to the parabolic mirror 11 are 45 degrees In other words, infrared rays are refracted at a right angle by the parabolic mirror 11. By making the incident rays to the parabolic mirror 11 parallel to the axis of vertical movement of the microscope, it is possible to make the optical system in which infrared rays are converged by the reflecting objective 13 unchanged irrespective of the vertical movement of the microscope, thereby preventing the great reduction of the infrared incidence efficiency with respect to the reflecting objective 13 which would be produced if the optical system changes with the vertical movement of the microscope.

The operation of the present invention for achieving the second object will be explained with reference to FIG. 4. The rays entering from the left side of a flat mirror 12 are parallel infrared rays with the frequency modulated by the interferometer of a Fourier transform infrared spectrometer. The infrared rays are converged on a sample by a parabolic mirror 11 and a Cassegrain type reflecting objective 5. Ultraviolet rays produced by a mercury lamp 1 is converged on the sample by a lens 6 and the Cassegrain type reflecting objective 5 in the same way with the case of the infrared rays. The infrared rays reflected by the sample is converged by the Cassegrain type reflecting objective 5. By the Fourier transformation of the signal received by an infrared detector 171 the infrared spectrum of the sample is measured. The fluorescence of the sample exited by ultra violet rays is converged by the Cassegrain type reflecting objective 5 and the rays dispersed by a detection auxiliary device 7 are received by a visible light detector 172, whereby the fluorescence spectrum is measured. The reference numeral 2 represents a selector mirror having a dichroic filter which reflects ultraviolet light but transmits visible light or infrared light. By inserting the selector mirror 2, it is possible to switch over from the measurement of infrared spectrum to the measurement of fluorescence spectrum. The reference numeral 3 also represents a selector mirror which has a function of separating transmitted rays from reflected rays. It is possible to measure fluorescence spectrum and infrared spectrum by the same apparatus by using the dichroic filters of the selector mirrors 2 and 3 for the measurement of fluorescence spectrum and using the partial mirror of the selector mirror 3 for the measurement of infrared spectrum. In the apparatus of the present invention, it is impossible to measure fluorescence spectrum and infrared spectrum at the same time. When fluorescence spectrum and infrared spectrum are measured separately, the order of measurement is not specified. However, since fluorescence has a higher sensitivity, it is better to identify a material by the fluorescence first and to measure the infrared spectrum thereafter in terms of the measuring speed. It is necessary that fluorescence is measured speedily, because some samples are discolored when it is irradiated with ultraviolet light, which is exciting light, for a long time.

The above and other objects, features and advantages of the present invention will become clear from the following description of the preferred embodiments thereof, taken in conjunction with the accompanying drawings.

BRIEF DESCRIPTION OF THE DRAWINGS

FIGS. 1a and 1b are sectional views of a first embodiment of an infrared microspectrometer according to the present invention, wherein FIG. 1a is an explanatory view of a spectrophotometer;

FIGS. 5 to 7 are explanatory views of a selector mirror of an infrared microspectrometer according to the present invention, wherein FIG. 7 shows the entire structure thereof;

FIG. 5 is an explanatory view of the portion C of the selector mirror shown in FIG. 7; and FIG. 6 is an explanatory view of the portions A and B of the selector mirror shown in FIG. 7;

DESCRIPTION OF THE PREFERRED EMBODIMENTS

First Embodiment

Figure 1A:
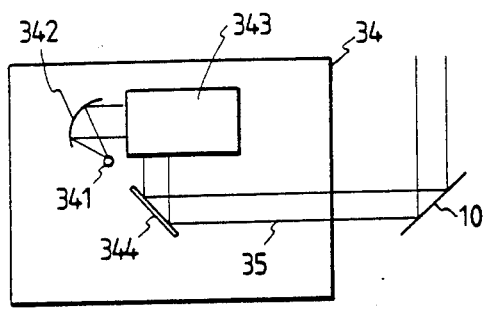
Figure 1B:
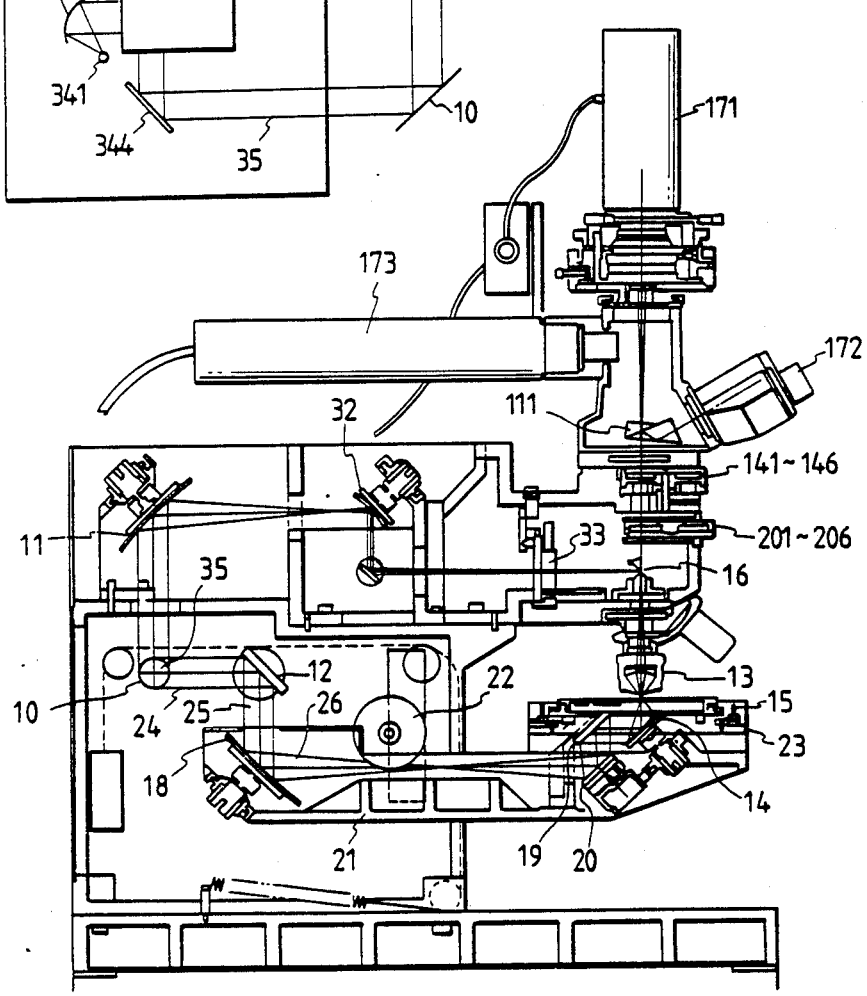

A first embodiment of the present invention will be explained hereinunder with reference to FIGS. 1a and 1b. FIG. 1b shows an apparatus which is capable of measuring the Fourier transform infrared spectrum of a sample in both a transmission measuring mode and a reflection measuring mode. A flat selector mirror 10 consists of two mirrors, namely, a reflecting mirror for directing parallel infrared rays from a Fourier transform infrared spectrometer toward a parabolic mirror 11 for measuring them in a transmission measuring mode, and a mirror for directing them toward a flat mirror 12 for measuring them in a reflection mode. These mirrors are switched by the operation of a lever.

An optical system of a transmission measuring mode will first be explained with reference to FIG. 1a, which is an explanatory view of the interior of a spectrophotometer 34 for supplying infrared rays 35 in the infrared microspectrometer shown in FIG. 1b. In FIG. 1a, the flat mirror 10 is provided in order to use the infrared rays 35 in a reflection mode. The parallel infrared rays 35 from the spectrophotometer 34 are converged on the first focal point of an ellipsoidal mirror 32 by the parabolic mirror 11. This operation is carried out by adjusting the focal point of the parabolic mirror 11 with accuracy on the preset optical axis by using an infrared detection plate, and thereafter adjusting a second focal point of the ellipsoidal mirror 32 to an aperture 33 by using an infrared detection plate. Similarly, the adjustments of the positions of an optical system which will be described hereinunder are carried out by using an infrared detection plate. In an edge mirror 16, the upper half portion is a mirror and the lower half portion is transparent. The infrared rays entering from the ellipsoidal mirror 32 are reflected toward a reflecting objective 13 by the edge mirror 16. The infrared rays reflected by a sample on a sample stage 15 pass through the back side of the edge mirror 16 and reach an infrared detector 171.

The interior of the spectrophotometer 34 will be explained in the following. As the spectrophotometer 34, a known spectrophotometer is usable. As shown in FIG 1a, the rays from a globar light source 341 are reflected by a parabolic mirror 342 so as to enter a Michelson interferometer 343, and the rays emitted therefrom are reflected by a selector mirror 344 to obtain parallel infrared rays with the frequency modulated.

The optical system of a transmission measuring mode will next be explained. The selector flat mirror 10 is switched so as to direct the parallel infrared rays 35 from the spectrophotometer 34 toward the flat mirror 12. The infrared rays 25 are then converged on the focal point having a longer focal length of the ellipsoidal mirror 14 by a parabolic mirror 18. In order to get a focal point having a shorter focal length on the sample stage 15, the optical path is raised by two flat mirrors 19 and 20. The parabolic mirror 18, the ellipsoidal mirror 14 and the two flat mirrors 19, 20 are mounted on a boat-shaped stage 21, and the sample stage 15 is fixed to the boat-shaped stage 21 by bolts. The boat-shaped stage 21 is moved by an up and down-drive unit 22 so as to enable focussing in both reflection mode and transmission mode.

The above-described structure enables the distance between the sample stage 15 and the reflecting objective 13 to be freely enlarged and even a large sample to be placed on the sample stage 15. Thus, it is possible to measure the reflected infrared spectrum of the surface of a microfine portion of a large sample, which is impossible in the prior art.

In the case of a transmission measuring mode, there is naturally a limitation in the thickness of a sample for spectral measurement. Particularly, in the case of infrared spectroscopy, the thickness of a sample is not more than 20 $\mu$m. Since an infrared wavelength itself is long, if the optical system is adjusted in advance so as to have a deep focal depth and at the highest sensitivity by vertically moving the sample stage, the degree of necessity for adjusting the focal point in accordance with different samples is small. In the case of measuring while changing the reflecting objective 13 for one having a different magnification, it is necessary to adjust the position of a converging mirror for infrared light illuminating from the lower portion every time the reflecting objective is changed because the focal length is different according to the magnification of the objective. This adjustment which is impossible in the prior art has been enabled by the present invention. The reference numerals 201 to 206 and 141 to 146 represent discs such as those shown in FIG. 9. The reference numeral 111 denotes a prism for distributing the analyzing rays which have been transmitted through the sample to the infrared detector 171, a visible light detector 173 or an eyepiece 172. Two triangular prisms are used in combination in this embodiment, but this prism is unnecessary for detection by the infrared detector 171.

Second embodiment

Figure 2:
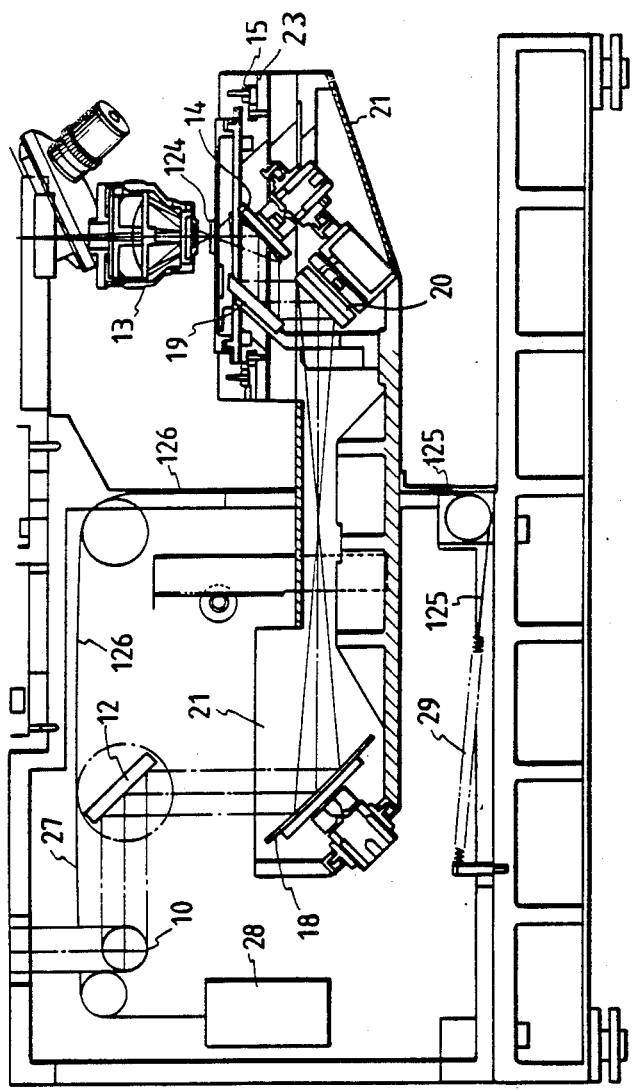
FIG. 2 is an enlarged view of a boat-shaped stage and a sample stage of an infrared microspectrometer according to the present invention.

A second embodiment of the present invention will here be explained with reference to FIG. 2, which is an enlarged view of a boat-shaped stage and a sample stage.

Blackened screens 125, 126 of stainless steel are attached to the upper limit and the lower limit, respectively, of the travel of a boat-shaped stage 21. A wire 27 is attached to one end of the upper screen 126 and a weight 28 is attached to the other end of the wire 27. A spring 29 is attached to the lower screen 125 on the underside of the boat-shaped stage 21 so as to vertically move in accordance with the vertical movement of the boat-shaped stage 21. The balance between both screens 125, 126 are kept, so that the vertical movement of the boat-shaped stage 21 is operated without a load.

In this way, it is possible to prevent the air or light outside the microscope from entering and to measure infrared spectrum without being influenced by vapor, carbon dioxide gas or the like and noise caused by external light.

Third embodiment

Figure 3:
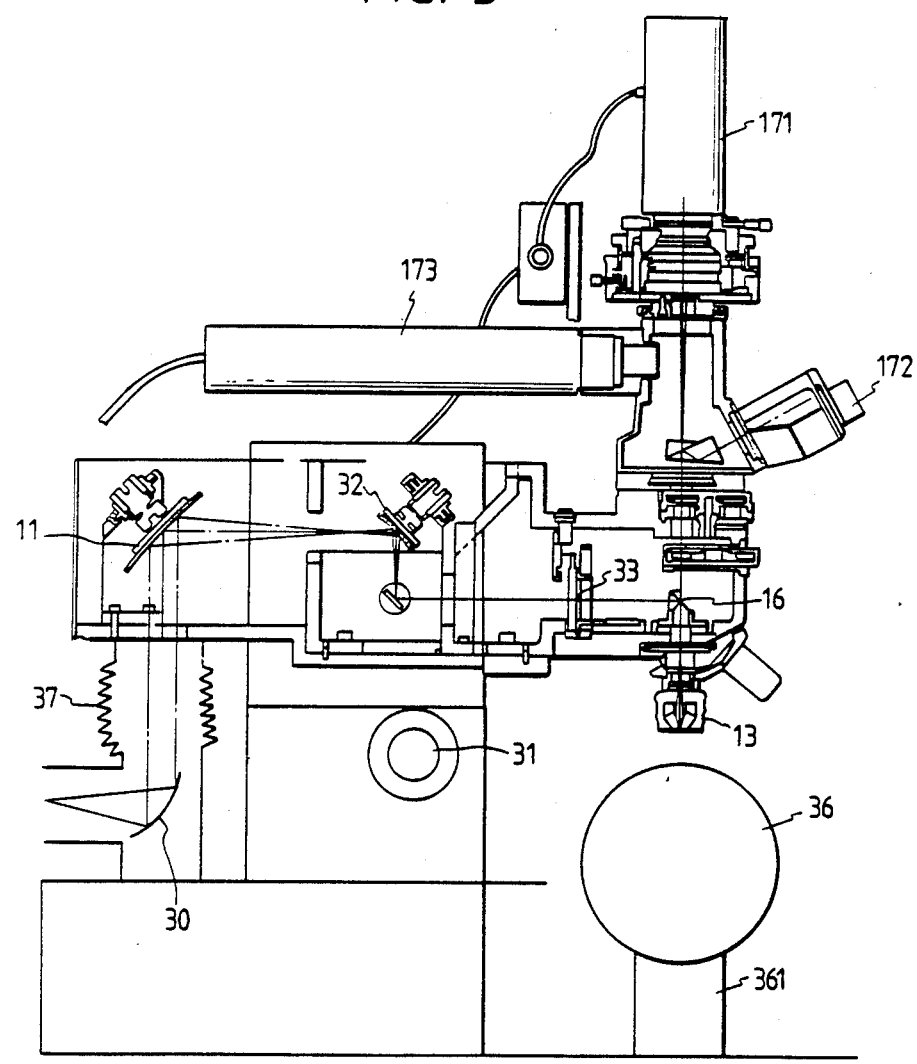
FIG. 3 is a sectional view of an infrared microspectrometer provided with a vertically movable microscope body.

A third embodiment of the present invention will be explained with reference to FIG. 3. In this embodiment, the microscope body is vertically moved. The infrared rays from a Fourier transform infrared spectrometer are converted into parallel rays by a parabolic mirror 30 so as to enter the parabolic mirror 11 and are converged on the first focal point of an ellipsoidal mirror 32 by the parabolic mirror 11. The infrared rays are then converged on the first focal point of an ellipsoidal mirror 32 by the parabolic mirror 11. The focal point of the parabolic mirror 11 is adjusted with accuracy on the preset optical axis, and thereafter a second focal point of the ellipsoidal mirror 32 is adjusted to an aperture 33 by using an infrared detection plate. In an edge mirror 16, the upper half portion is a mirror and the lower half portion is transparent. The infrared rays entering from the ellipsoidal mirror 32 are reflected toward a reflecting objective 13 by the edge mirror 16. The infrared rays reflected by a sample 36 placed on a sample stage 361 pass through the back side of the edge mirror 16 and reach an infrared detector 171.

The parabolic mirror 30 for converging the infrared rays from the Fourier transform infrared spectrometer is attached to a microscope stand. The microscope is vertically moved with respect to the microscope stand by a driving device 31. A rubber cylinder 37 having a configuration of a bellows is inserted between the parabolic mirror 30 and the parabolic mirror 11 so as to prevent external air and light from entering.

The above-described structure makes it possible to provide a wide space under the reflecting objective of the microscope therefore, so that it is possible to measure the infrared spectrum of the surface of a microfine portion of a sample of any size only if an appropriate sample holder is prepared.

According to this embodiment, it is possible to keep a large space under the reflecting objective of the microscope therefore, spectral measurement is enabled without any limitation in the size of a sample. In addition, even when the reflecting objective is changed, it is possible to immediately adjust the optical system to the position producing the correct focal length. It is therefore possible to measure infrared spectrum of a microfine portion with a high sensitivity by a simple operation.

Embodiments of an infrared microspectrometer for enhancing the accuracy of identification of the chemical species of a microfine portion will be explained hereinunder.

Fourth embodiment

Figure 7:
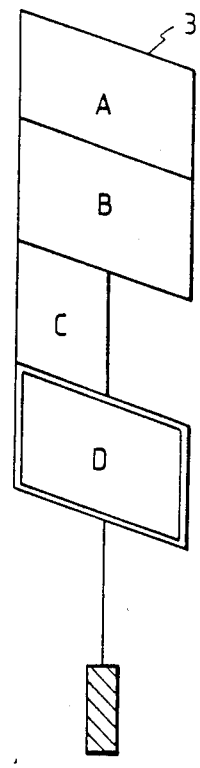
Figure 8:
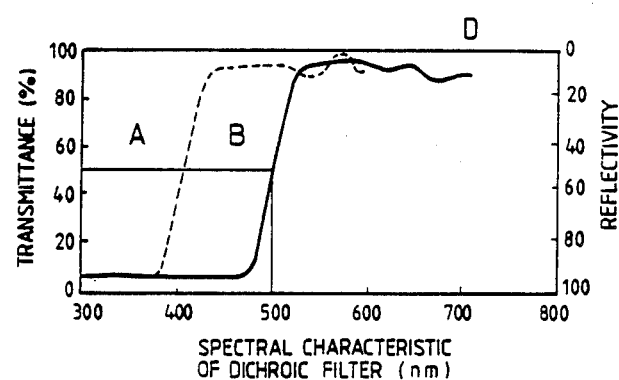
FIG. 8 shows the spectral characteristic of a dichroic filter used in the present invention.

A fourth embodiment of the present invention will be explained with reference to FIG. 4. The reference numeral 12 represents a flat mirror for introducing the parallel infrared rays 4 from the interferometer of a Fourier transform infrared spectrometer to a parabolic mirror 11. The infrared rays are converged on the second focal point of a Cassegrain type objective 5 by the parabolic mirror 11. In other words, the parabolic mirror 11 and the Cassegrain type objective 5 are so arranged as to have the focal point of the former agree with the second focal point of the latter. The reference numeral 1 denotes a high-pressure mercury lamp, and 6 a filter for cutting off visible light. The filter 6 is removable. When a sample is observed by visible light, the filter 6 is replaced by a filter for cutting off ultraviolet light. The reference numeral 130 represents a condenser lens for condensing the ultraviolet rays from the high-pressure mercury light 1 on the second focal point of the Cassegrain type objective 5. The reference numeral 3 denotes a selector mirror having a function of separating transmitted light from reflected light. The mirror system has the structure shown in FIG. 7. The portions A and B are a dichroic filter such as that shown in FIG. 6, and the spectral characteristic thereof is shown in FIG. 8. More specifically, at the portion B, the reflectivity of light of a short wavelength such as ultraviolet light is large but the reflectivity of light of a long wavelength such as visible light is very small and the transmittance is therefore large. If a mirror having the characteristic B is used, only ultraviolet light, which is exciting light, is reflected and projected to a sample, and since the fluorescence emitted from the sample is visible light, it is transmitted but ultraviolet light, which is an obstacle for the measurement of fluorescence, is not transmitted. Since visible light is necessary for observing the sample, a mirror having the characteristic A is used for observing the image of the sample.

Figure 5:
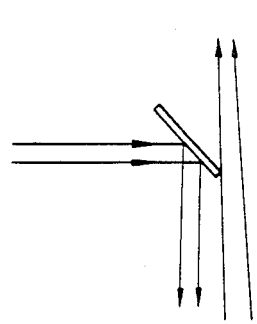

The portion C is a mirror shown in FIG. 5., which is used for measuring infrared spectrum. The mirror C is disposed in the optical system so that although the infrared rays projected to a sample are reflected by the mirror C, the infrared rays reflected by the sample passe through the back side of the mirror C. The portion D transmits all light. The angle of inclination of these mirrors with respect to the optical axis is about 45 degrees. A selector mirror 2 is a mirror for switching over between the measurement of infrared spectrum and the measurement fluorescence spectrum. The switching operation is conducted by inserting the selector mirror 2 in the optical path of infrared light. The selector mirror 2 has the same structure as that shown in FIG. 7 with the portion C removed therefrom.

Figure 9:
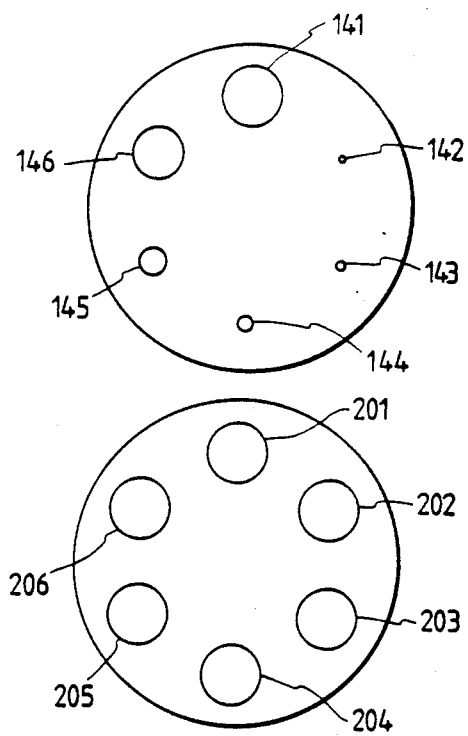
FIG. 9 is an explanatory view of a detection auxiliary device of an infrared microspectrometer according to the present invention.

The reference numeral 7 represents a detection auxiliary device which consists of two discs shown in FIG. 9. The reference numeral 141 and 201 denote holes of 10 mm in diameter. At the centers of circles 142 to 146, holes having diameters of 0.125 mm, 0.25 mm, 0.5 mm, 1.0 mm and 1.5 mm, respectively, are formed. These holes cut off the light at the background of the image of a sample which is a cause of noise. The reference numerals 202 to 206 denote interference filters which pass visible light of a specified wavelength alone therethrough. The wavelengths of visible light which can pass through the five interference filters 202 to 206 are different from each other. These filters have a function of cutting off the light of a wavelength which is unnecessary for observation. The respective discs are rotated separately from each other to select the appropriate hole diameter and filter. The reference numeral 173 represents a visible light detector serving also as a camera tube, and 171 an infrared detector. The reference numeral 40 represents a selector mirror for switching over between the infrared detector 171 and the visible light detector 173. A mirror system 41 is used for visually observing a sample 85 through eye piece 172.

Figure 4:
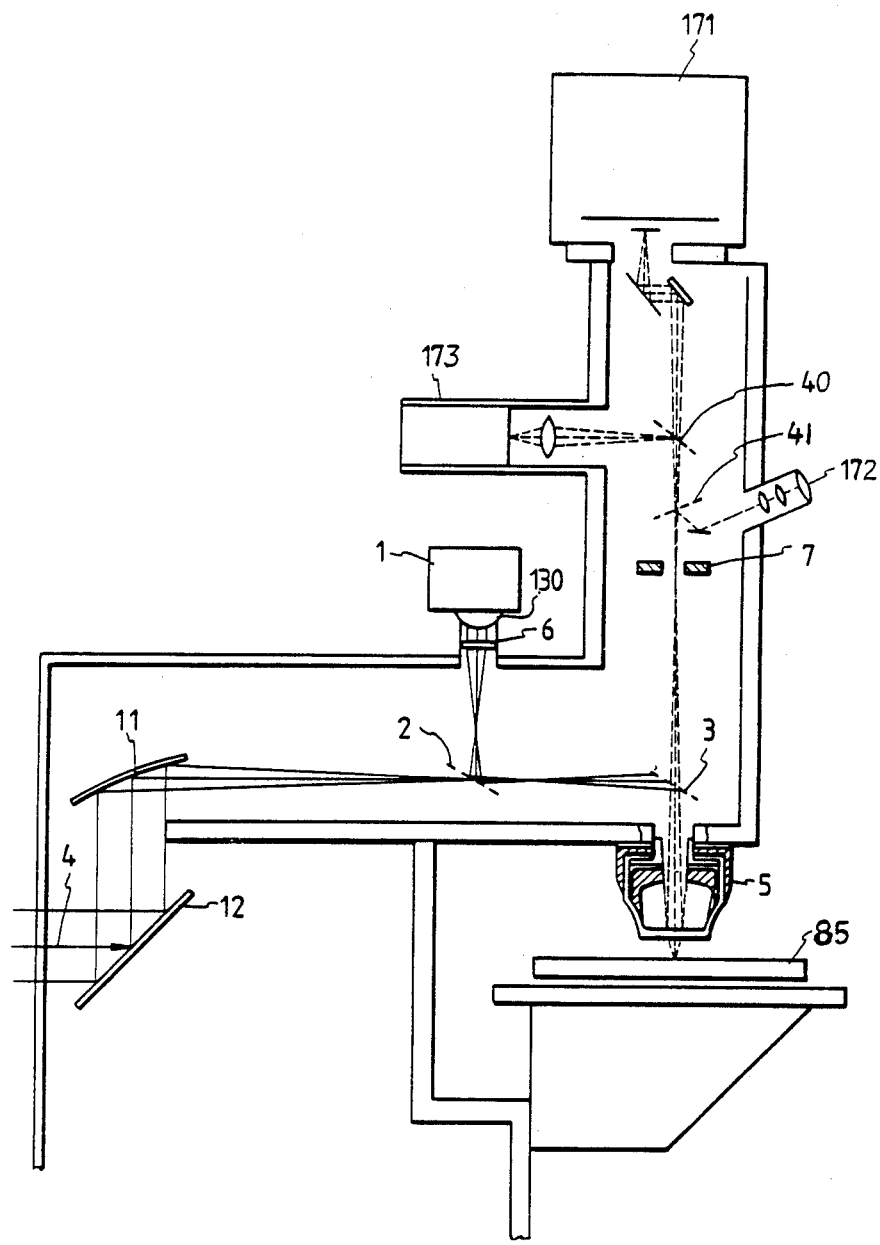
FIG. 4 is a sectional view of an infrared microspectrometer which is capable of projecting to a sample not only infrared rays but also ultraviolet rays from a high-pressure mercury lamp.

In the present invention, the interferometer of a Fourier transform infrared spectrometer and a computer for processing data are necessary in addition to the above-described elements, but these are omitted in FIG. 4.

The above-described structure is effective for facilitating the switching over between the measurement of infrared spectrum and fluorescence spectrum and the observation of the image of a sample in one apparatus by simultaneously operating the switching levers of the mirrors 2 and 3.

Fifth embodiment

A fifth embodiment of the present invention will now be explained with reference to FIGS. 10 and 11. This embodiment is characterized by a selector mirror 3 and the other structure is the same as that of the fourth embodiment.

Figure 6:
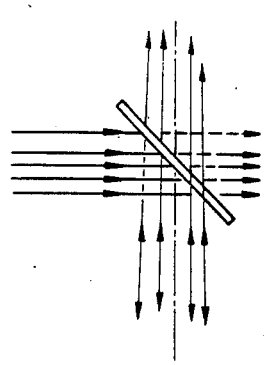

The portions A and B are a dichroic filter such as that shown in FIG. 6 and the spectral characteristic thereof is such as that shown in FIG. 8. In the vicinity of the end portion B in FIG. 10, the reflectivity of light having a short wavelength such as ultraviolet light is large, but the reflectivity of light of a long wavelength such as visible light is very small and the transmittance is therefore large. If a dichroic mirror having the characteristics indicated by the curve B in FIG. 11 is used, only ultraviolet light, which is exciting light, is projected to a sample, and since the fluorescence emitted from the sample is visible light, it is transmitted but ultraviolet light, which is an obstacle for the measurement of fluorescence, is not transmitted. When the wavelength of exciting ultraviolet light is short, the wavelength of the emitted fluorescence is also short, thereby involving a fear of the fluorescence also being cut off when measured by using the vicinity of the end portion B in FIG. 10. In such case, it is possible to move the point of application of light by the operation of a lever to a portion on the side of the end portion A at which the conditions for both exciting light and fluorescence are satisfied. Visible light is necessary for observation of a sample. For this purpose, the vicinity of the end portion A in FIG. 10 is used.

Figure 10:
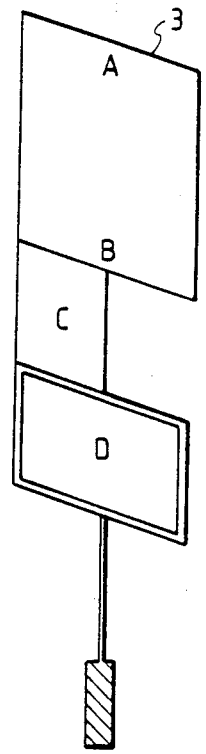
FIG. 10 shows the structure of another selector mirror.
Figure 11:
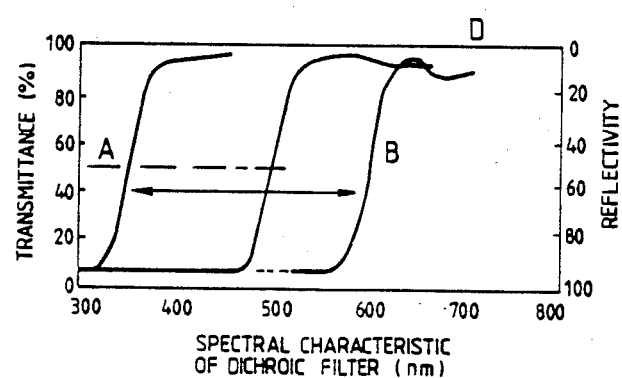
FIG. 11 shows the spectral characteristic of the portions A and B of the selector mirror shown in FIG. 10.

The portion C shown in FIG. 10 is a mirror shown in FIG. 5., which is used for measuring infrared spectrum The mirror C is disposed in the optical system so that although the infrared rays projected to a sample are reflected by the mirror C, the infrared rays reflected by the sample pass through the back side of the mirror C. The portion D shown in FIG. 10 transmit all light. The angle of inclination of these mirrors with respect to the optical axis is about 45 degrees.

The switching operation between the measurement of infrared spectrum and fluorescence spectrum is conducted by inserting a selector mirror 2 in the optical path of infrared light. The selector mirror 2 has the same structure as that shown in FIG. 10 which the portion C removed therefrom.

Sixth embodiment

A sixth embodiment will be explained with reference to FIG. 12. In this embodiment, a light source for measuring fluorescence is provided on a vertically movable sample stage.

Figure 12:
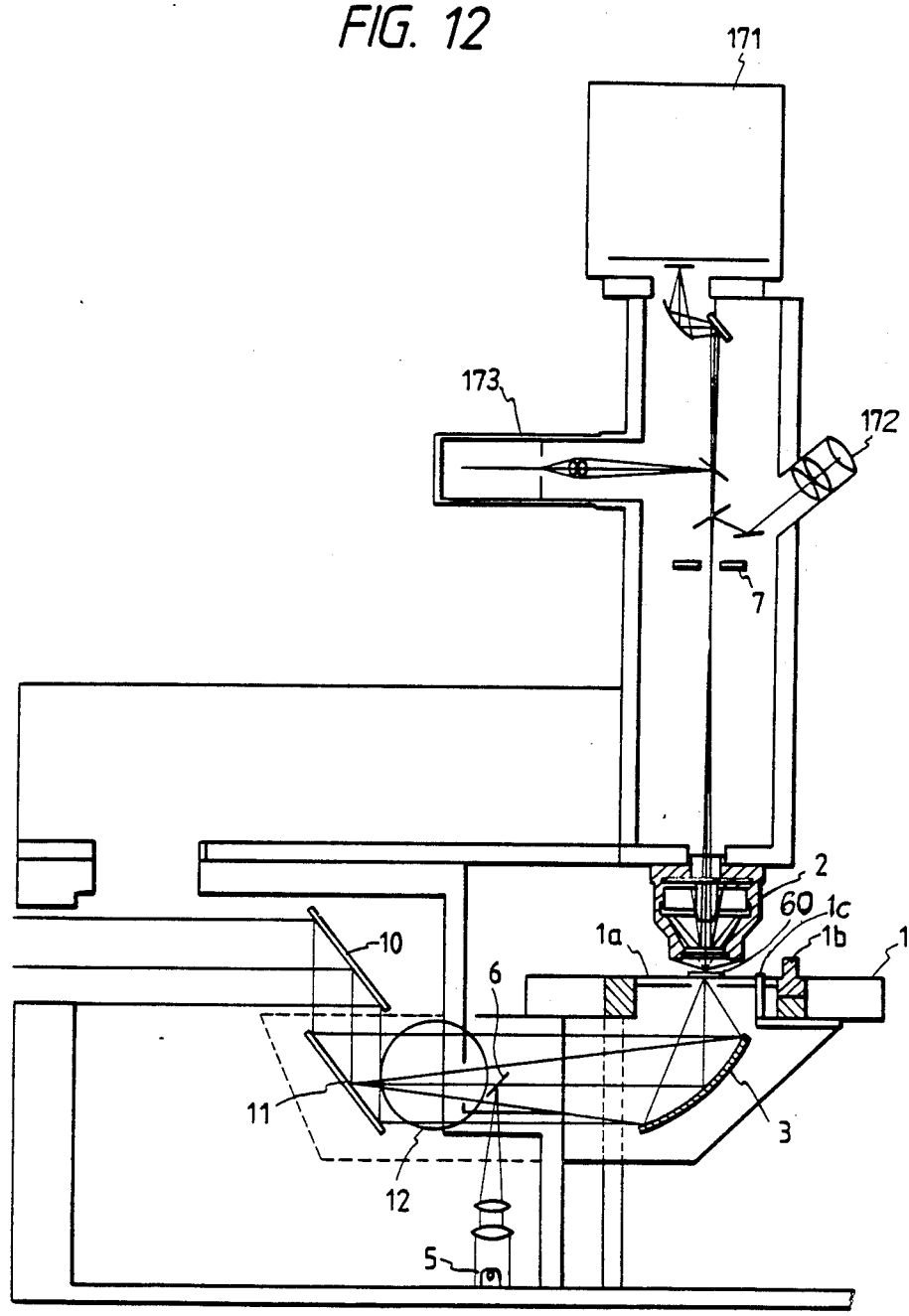
FIG. 12 is a sectional view of an infrared microspectrometer of a transmission measuring mode provided with a light source for measuring fluorescence on the side of the vertical movable sample stage.

FIG. 12 shows the main part of the structure of an infrared microspectrometer of this embodiment. The reference numerals 10 and 11 represent flat mirrors which are arranged such that the parallel infrared rays emitted from the interferometer (not shown) of a Fourier transform infrared spectrometer are projected to a converging mirror 3. The reference numeral 12 represents an up and down-drive unit of the converging mirror 3. The converging mirror 3 and the flat mirror 11 in combination are simultaneously vertically moved by the up and down-drive unit 12. The reference numerals 173, 172 and 171 denote an eyepiece, a TV monitor and an infrared detector, respectively. The converging mirror 3 is a parabolic mirror having a short focal length and is used at an angle of deviation of 90 degrees. An XYZ stage 1 is so designed that a sample table 1a is vertically moved by rotating a rotor 1. A selector mirror 6 is a flat mirror for projecting the visible light from a tungsten lamp 5 to an objective 2 and visible light is projected by inserting the selector mirror 6 in the optical path by operating a lever. The reference numeral 7 denotes a detection auxiliary device which consists of a combination of two discs such as those shown in FIG. 9. It goes without saying that a high-pressure lamp may be used as a source of projection in place of the tungsten lamp 5.

When infrared spectrum is measured by using this apparatus, infrared rays are first passed through the converging mirror 3 through the flat mirrors 10 and 11, and the up and down-drive unit 12 is operated so as to maximize the intensity of the infrared light received by an infrared detector 15 while adjusting the height of the XYZ stage 1. The selector mirror 6 is next switched in order that the visible light from the tungsten lamp 5 enters the objective 2 through the converging mirror 3. A sample 60 is placed on the sample table 1a. The rotor 1b is rotated with the knob so as to vertically move the sample table 1a and the XY axis is moved to focus on the point of measurement of the sample. The selector mirror 6 is next removed and the rotor 1b is rotated so that the intensity of the infrared light received by the infrared detector 171 is maximum, and the rotation of sample table 1a is fixed by a pin 1c.

Figure 13:
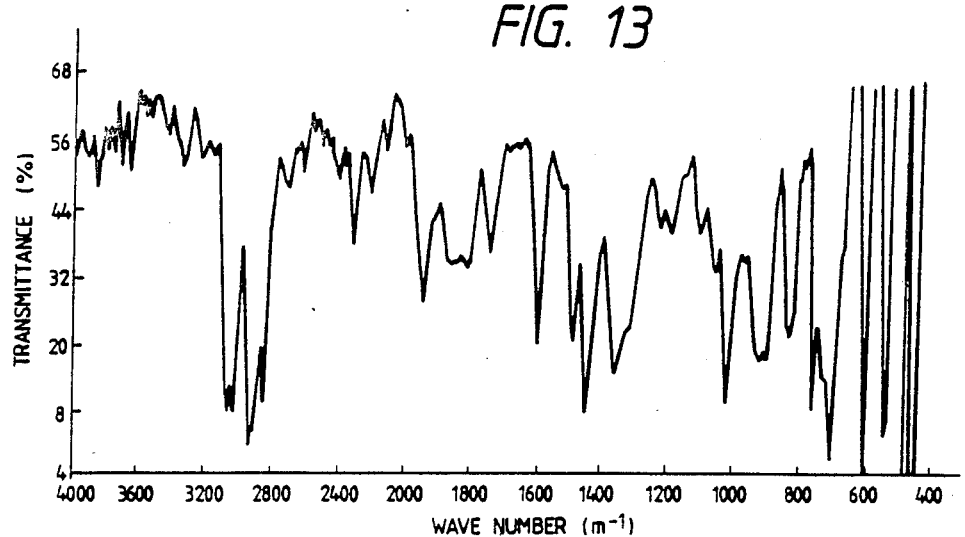
FIG. 13 shows an example of the infrared spectra obtained by the infrared microspectrometer shown in FIG. 12.
Figure 14:
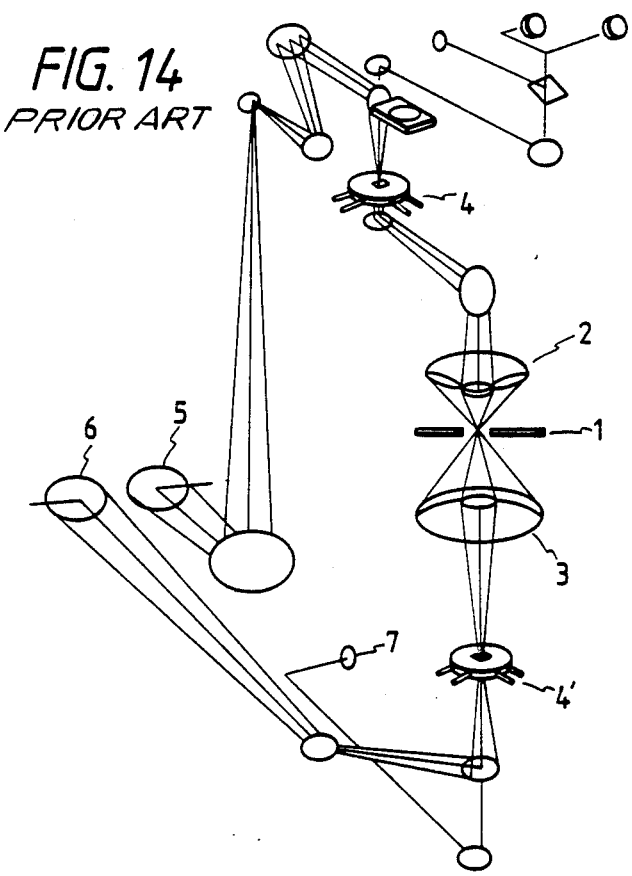
FIGS. 14 and 15 are explanatory views of a conventional infrared spectrum measuring apparatus.
Figure 15:
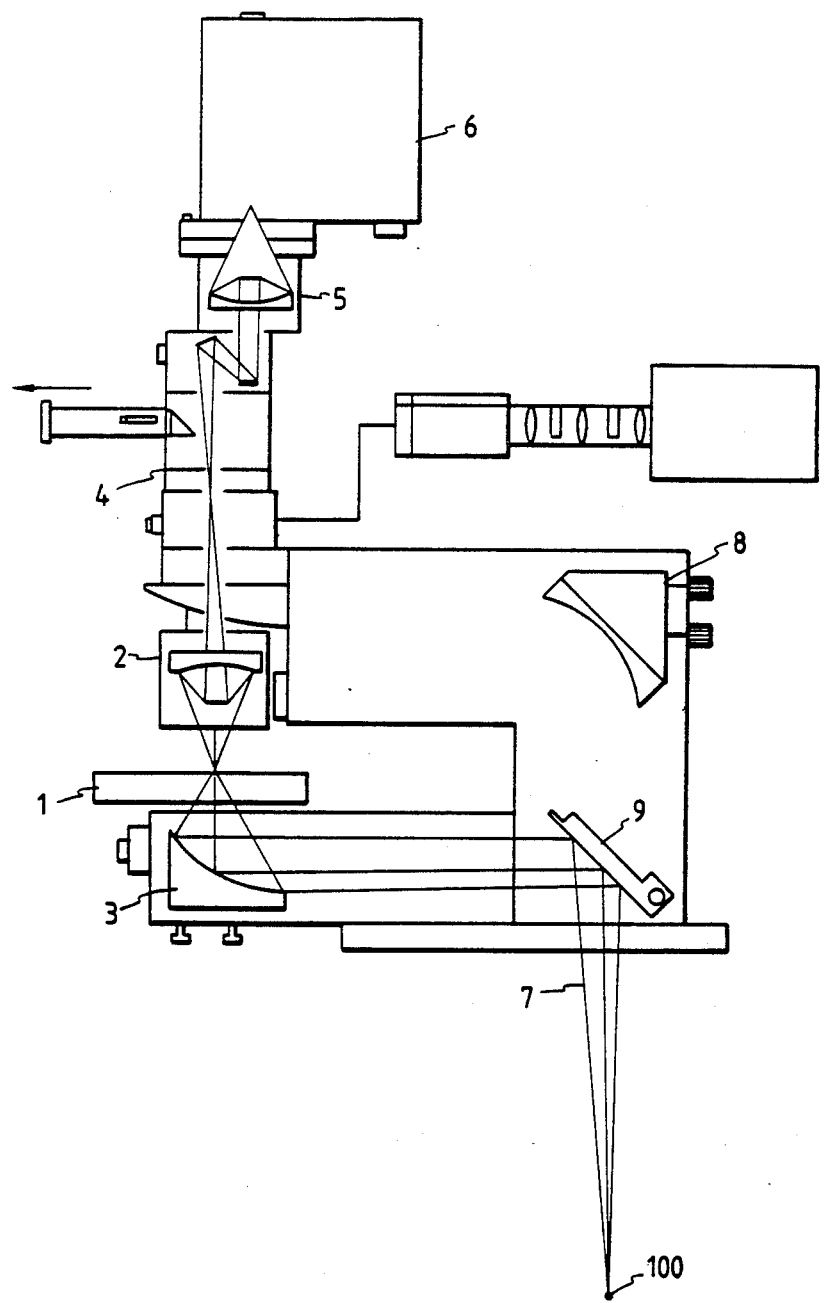

The results of measurement by such operation are shown FIG. 13. The infrared spectrum of polystyrene having a particle diameter of 5 $\mu$m was measured by using an objective having a magnification of 52 times and a stop of 4 $\mu$m$\phi$ and at an accumulation of 2,000 times. The abscissa represents a wave number and the ordinate a transmittance (%).

As described above, according to the apparatus of this embodiment, it is possible to agree the point of measurement of any sample with the focal point of infrared light, thereby realizing a high-accuracy infrared microspectrometer. In other words, this embodiment enables the focal point of a converging mirror, the focal point of an objective and the point of measurement of any sample to constantly agree with each other, thereby enabling the measurement of the infrared spectrum of a microfine portion of any sample to have a measurable thickness of 5 to 20 μm.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An infrared microspectrometer for spectral measurement in a transmission or reflection mode comprising: a spectrophotometer; a microscope; a detector; and a vertically movable sample stage having a first optical means for converting analyzing rays into parallel rays between the light source of said spectrophotometer and said sample stage and a second optical means for receiving said rays from said first optical means and projecting said rays to a sample.

2. An infrared microspectrometer according to claim 1, wherein each of said first optical means and said second optical means is composed of a parabolic mirror.

3. An infrared microspectrometer according to claim 1, wherein said second optical means is composed of a parabolic mirror and an ellipsoidal mirror.

4. An infrared microspectrometer for spectral measurement in a transmission mode according to claim 3, wherein said second optical means is composed of a parabolic mirror, an ellipsoidal mirror and at least two flat mirrors provided between said parabolic mirror and said ellipsoidal mirror.

5. An infrared microspectrometer according to claim 1, wherein the optical axis of said rays entering from said first optical means to said second optical means is parallel to the moving axis of said vertically movable sample stage.

6. An infrared microspectrometer according to claim 1, wherein said vertically movable stage is provided with a vertically movable screen for preventing external air and light from entering said stage.

7. An infrared microspectrometer for spectral measurement in a reflection mode comprising: a spectrophotometer; a fixed sample stage; a vertically movable objective; a detector; a first optical means for converting analyzing rays into parallel rays between the light source of said spectrophotometer and said vertically movable objective; and a second optical means for receiving said rays from said first optical means and projecting said rays to a sample; wherein the optical axis of said parallel rays is parallel to the optical axis of the rays projected from said second optical means to said sample.

8. An infrared microspectrometer according to any of claims 1 to 7, wherein said spectrophotometer is a Fourier transform infrared spectrometer.

* * * * *

UNITED STATES PATENT AND TRADEMARK OFFICE
CERTIFICATE OF CORRECTION

Page 1 of 2

PATENT NO. : 4,922,104
DATED : 1 May 1990
INVENTOR(S) : Kinya EGUCHI et al.

It is certified that error appears in the above-identified patent and that said Letters Patent is hereby corrected as shown below:

| Column | Line | |
|---|---|---|
| TITLE PAGE: | | Change inventor "Shigeru Wakena" to --Shigeru Wakana--. |
| | | After "[73] Assignee:" delete "501". |
| ABSTR. | 7 | Change "microspectometer" to --microspectrometer--. |
| 1 | 55 | After "infrared" insert --rays--. |
| 4 | 51 | Change "is" to --be--. |
| 4 | 52 | Change "it is" to --they are--. |
| 6 | 11 | Change "globar" to --global--. |
| 8 | 50 | Change "passe" to --pass--. |
| 8 | 56 | After "measurement" insert --of--. |
| 9 | 64 | Change "transmit" to --transmits--. |

UNITED STATES PATENT AND TRADEMARK OFFICE
CERTIFICATE OF CORRECTION

PATENT NO. : 4,922,104

DATED : May 1, 1990

INVENTOR(S) : Kinya Eguchi et al

It is certified that error appears in the above-identified patent and that said Letters Patent is hereby corrected as shown below:

| Column | Line | |
|--------|------|---|
| 10 | 3 | Change "which" to --with--. |
| 10 | 53 | Before "sample" insert --the--. |
| 10 | 62 | Delete "agree" and insert therefor --cause--. |
| 10 | 63 | After "sample" insert --to coincide--. |
| 10 | 68 | Replace "agree" with --coincide--; after "with" delete "each other" and insert --one another--. |

Signed and Sealed this

Twenty-seventh Day of August, 1991

Attest:

HARRY F. MANBECK, JR.

Attesting Officer

Commissioner of Patents and Trademarks